(12) United States Patent
Wynn

(10) Patent No.: US 9,404,849 B2
(45) Date of Patent: Aug. 2, 2016

(54) MICRO VOLUME INLINE OPTICAL SENSOR

(71) Applicant: Endress+Hauser Conducta Inc., Anaheim, CA (US)

(72) Inventor: William H. Wynn, Hillsborough, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 404 days.

(21) Appl. No.: 13/780,766

(22) Filed: Feb. 28, 2013

(65) Prior Publication Data

US 2014/0240701 A1    Aug. 28, 2014

(51) Int. Cl.
*G01N 21/05*    (2006.01)

(52) U.S. Cl.
CPC .................................. *G01N 21/05* (2013.01)

(58) Field of Classification Search
CPC ....................................................... G01N 21/05
USPC ................... 356/244–246; 250/373, 573–577
See application file for complete search history.

(56) References Cited

U.S. PATENT DOCUMENTS

| | | | |
|---|---|---|---|
| 3,810,695 A | 5/1974 | Shea | |
| 4,988,155 A * | 1/1991 | Harner et al. | 385/12 |
| 5,808,737 A * | 9/1998 | Edens et al. | 356/246 |
| 5,905,271 A | 5/1999 | Wynn | |
| 6,512,223 B1 | 1/2003 | Wynn | |
| 6,977,365 B1 | 12/2005 | Wynn | |
| 2010/0269940 A1 | 10/2010 | Wynn et al. | |
| 2012/0061579 A1 | 3/2012 | Wynn | |
| 2012/0119101 A1 | 5/2012 | Wynn | |

FOREIGN PATENT DOCUMENTS

| | | |
|---|---|---|
| EP | 0089157 A1 | 9/1983 |
| EP | 1818666 A1 | 8/2007 |

OTHER PUBLICATIONS

McGrosky, Dale, "Introduction to O-rings", revised Feb. 2013, Satori Seal Corporation.*

* cited by examiner

*Primary Examiner* — Rebecca C Bryant
(74) *Attorney, Agent, or Firm* — Edward S. Wright

(57) ABSTRACT

Micro volume inline optical sensor comprising a flowcell having a sample chamber which has a volume less than 0.4 mL and increases in diameter from two ends toward the middle, a flow passageway intersecting the chamber where the diameter is the greatest, monitoring ports with optically transmissive windows at the ends of the chamber, mounting rings on opposite sides of the flowcell disposed coaxially of an optical axis that passes through the monitoring ports and the sample chamber, and a light source and an optical detector mounted on the mounting rings in alignment with each other along the optical axis. In one embodiment, the sample chamber has a side wall with oppositely inclined frusto-conical sections, and the ends of the chamber are closed and sealed by the monitoring port windows and O-ring gaskets that surround the open ends and are compressed between the body of the flowcell and the windows.

19 Claims, 2 Drawing Sheets

MICRO VOLUME INLINE OPTICAL SENSOR

BACKGROUND OF THE INVENTION

1. Field of Invention

This invention pertains generally to inline optical sensors and, more particularly, to a micro volume inline optical sensor.

2. Related Art

Inline optical sensors for monitoring the properties of product streams in biotechnology and other sanitary applications commonly include flowcells with sample cavities, flow passageways for delivering product samples to and from the sample cavities, and light sources and detectors on opposite sides of the cavities for measuring the optical properties of product samples in the cavities.

The flow lines employed in such applications typically have internal diameters ranging in size from about 1/16 inch to about 3/4 inch (approximately 1.6 mm to 19 mm), with the smaller flow lines being found primarily in laboratories and small scale processes, where there is a need for sample cells having smaller volumes.

With the smaller product lines and flow passageways, however, drainage can be a problem even if the flowcells are oriented with the passageways extending vertically, and liquid holdup and air pockets in the sample cavities can also be a problem.

OBJECTS AND SUMMARY OF THE INVENTION

It is, in general, an object of the invention to provide a new and improved micro volume inline optical sensor.

Another object of the invention is to provide a micro volume inline optical sensor of the above character which overcomes limitations and disadvantages of inline sensors and flowcells heretofore provided.

These and other objects are achieved in accordance with the invention by providing a micro volume inline optical sensor comprising a flowcell having a sample chamber which has a volume less than 0.4 mL and increases in diameter from two ends toward the middle, a flow passageway intersecting the chamber where the diameter is the greatest, monitoring ports with optically transmissive windows at the ends of the chamber, mounting rings on opposite sides of the flowcell disposed coaxially of an optical axis that passes through the monitoring ports and the sample chamber, and a light source and an optical detector mounted on the mounting rings in alignment with each other along the optical axis.

In one presently preferred embodiment, the sample chamber has a side wall with oppositely inclined frusto-conical sections, and the ends of the chamber are closed and sealed by the monitoring port windows and O-ring gaskets that surround the open ends and are compressed between the body of the flowcell and the windows.

DETAILED DESCRIPTION

Figure 1:
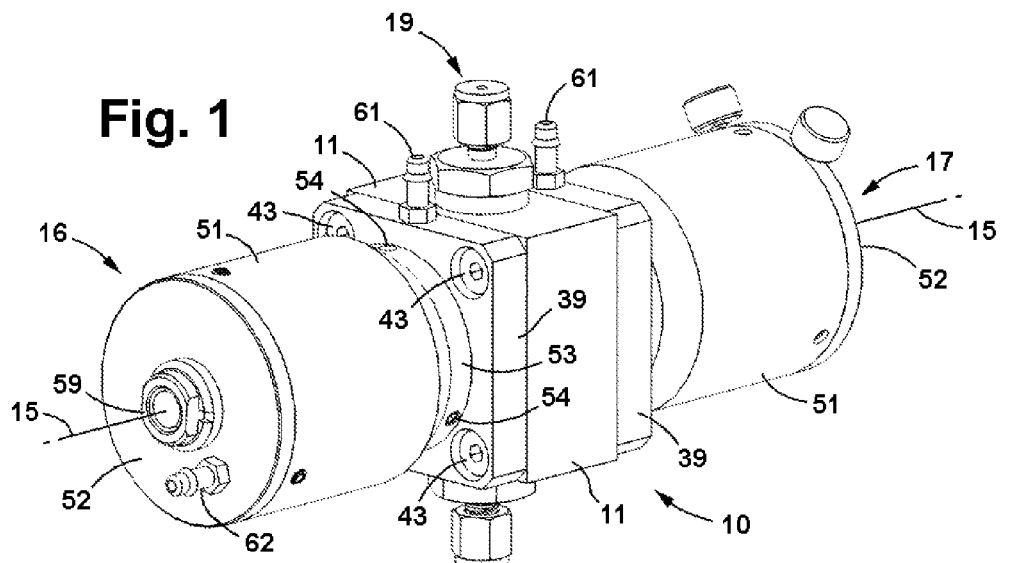
FIG. 1 is an isometric view of one embodiment of a micro volume inline optical sensor Incorporating the invention.
Figure 2:
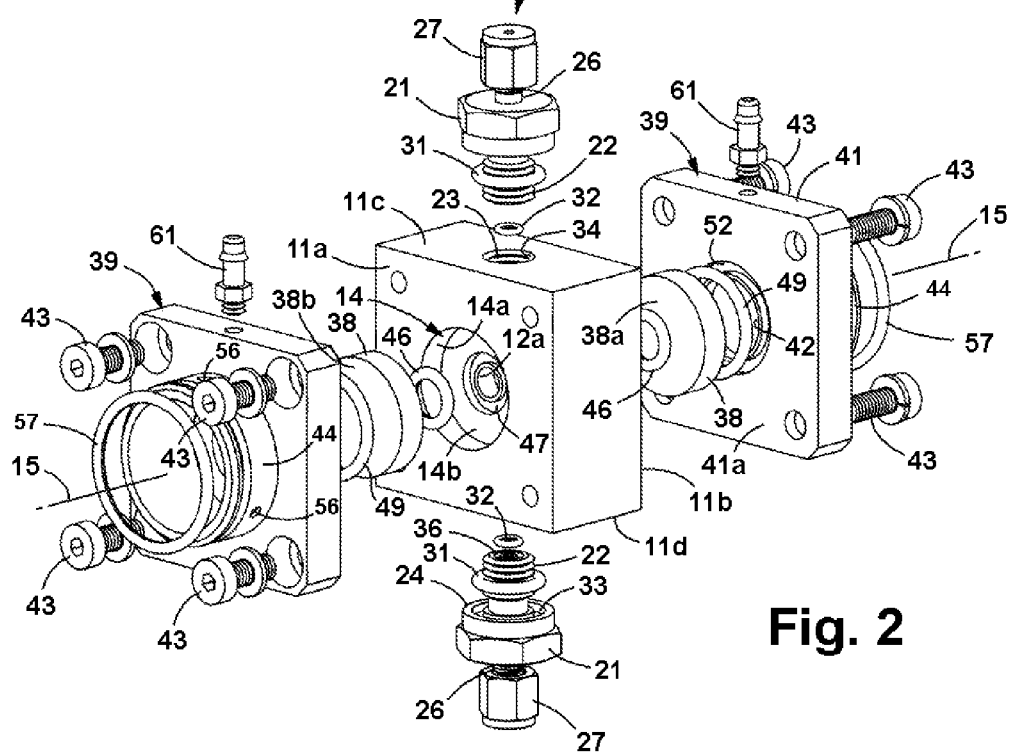
FIG. 2 is an exploded isometric view of the embodiment of FIG. 1.
Figure 3:
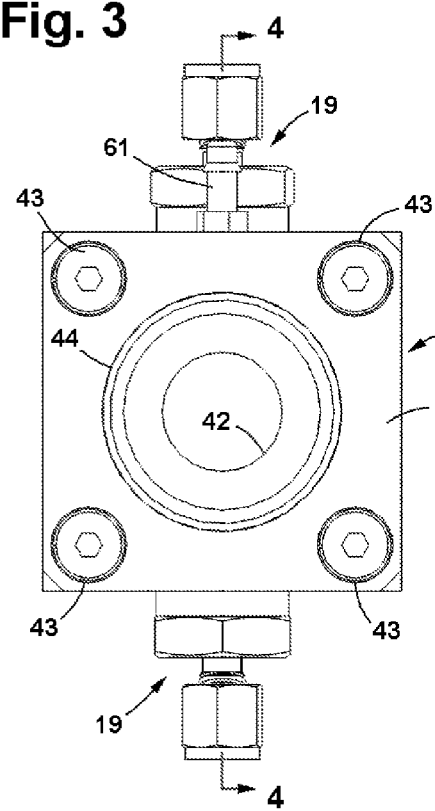
FIG. 3 is an end elevational view of the embodiment of FIG. 1.
Figure 4:
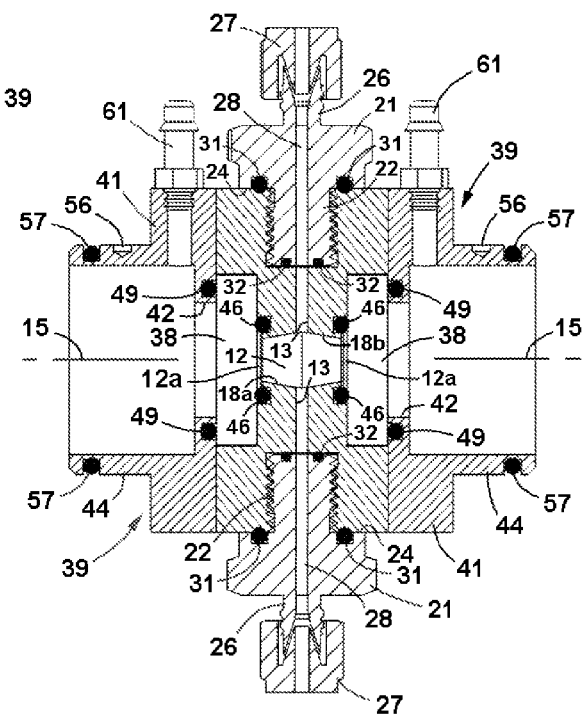
FIG. 4 is a cross-sectional view taken along line 4-4 in FIG. 3.

As illustrated in the drawings, the micro volume inline optical sensor includes a flowcell 10 which has a rigid body or block 11 fabricated of a material such as stainless steel with a sample cavity or chamber 12 and a flow passageway 13 formed therein. Monitoring ports 14, 14 open through opposite sides 11a, 11b of the block and are aligned along an optical axis 15 which passes through the chamber. A light source 16 and detector 17 are mounted on the block in alignment with the optical axis, with light from the source passing through the sample chamber to the detector.

Monitoring ports 14 have cylindrical side walls 14a, 14a and annular inner or rear walls 14b, 14b which are centered about the optical axis. The chamber has open ends 12a, 12a that face the monitoring ports and open through the rear walls of the ports.

Figure 5:
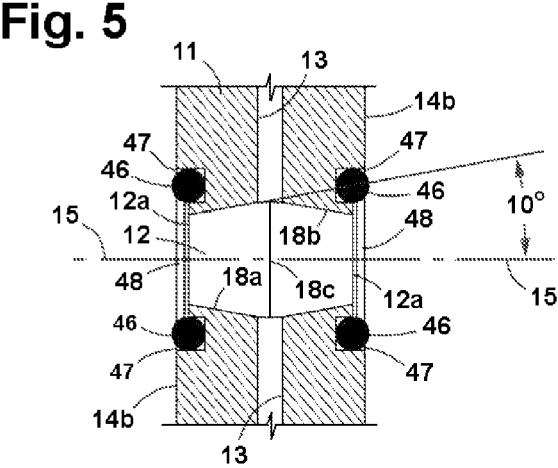
FIG. 5 is an enlarged fragmentary view of an area of FIG. 4.

Chamber 12 has a side wall 18 with two frusto-conical sections 18a, 18a which are disposed coaxially of the optical axis and increase in diameter from the ends of the chamber toward the center, coming together at a junction 18c in a radial plane midway between the ends. In the embodiment illustrated, the two sections are inclined at an angle of 10 degrees to the optical axis, as best seen in FIG. 5.

Flow passageway 13 extends in a direction generally perpendicular to optical axis 15, opening through the upper and lower sides 11c, 11d of the body and intersecting chamber 12 at the center where the diameter is the greatest. This significantly reduces the possibility of air becoming entrapped in the optical path and degrading the measurements and also ensures proper drainage from the cell.

Stainless steel ISO Fittings 19 are threadedly mounted on the body at the outer ends of the flow passageway for connecting flow lines to the flowcell. These fittings have a body with central section 21 of relatively large diameter and an externally threaded section 22 of reduced diameter that extends from one end of the central section and is received in an internally threaded counterbore 23 at the end of the flow passageway in the flowcell body, with an annular shoulder 24 between the two sections. A stem 26 extends from the other end of central section 21, and a connector 27 is threadedly mounted on the outer portion of the stem for connection to a product line. The fitting has a passageway 28 which is aligned axially with and of the same diameter as flow passageway 13.

Sealing between the fittings and the flowcell body is provided by O-ring gaskets 31, 32 which are received in seats formed in the fittings and in the flowcell body. Gasket 31 surrounds the threaded section of the fitting and is received in aligned seats 33, 34 formed in shoulder 24 and in the upper and lower sides 11c, 11d of the flowcell body. Gasket 32 surrounds the flow passageway and is disposed in a groove or seat 36 in the tip of threaded section 22. The gaskets are under controlled compression when the fittings are tightened to bring shoulders 24 into firm contact with the upper and lower surfaces of the flowcell body. The controlled compression provides tight seals and ensures that the integrity of the seals will be maintained, even during repeated CIP and SIP cleaning cycles.

The ISO fittings are interchangeably mounted on the flowcell body and are available in various sizes and types, which allows the flowcell to be used with lines of different sizes and different materials such as stainless steel, Teflon®, nylon, and Tygon®.

Optically transparent windows 38, 38 are mounted in monitoring ports 14, 14 and retained in position by mounting rings 39, 39 fabricated of a material such as stainless steel. The windows have solid cylindrical bodies fabricated of quartz with a diameter slightly less than the cylindrical side walls 14a of the ports, and the mounting rings have generally square bases 41 with apertures 42 of lesser diameter than the windows. The mounting rings are attached to opposite sides 11a, 11b of the flowcell body by mounting screws 43 and have cylindrical mounting flanges 44 for the light source and detector on the outer sides thereof.

The open ends of chamber 12 are closed and sealed by windows 38, 38 and by O-ring gaskets 46, 46 between the inner faces 38a of the windows and the rear walls 18b of the monitoring ports. These gaskets are received in O-ring grooves or seats 47, 47 which are formed in the rear walls of the ports and surround the open ends of the chamber. As best seen in FIG. 5, an annular section of the wall between the gasket seat and the chamber is cut away to a depth of approximately one-half of the depth of the seat such that the liquid side of the gasket is exposed to the liquid in the chamber through an open area 48 to allow CIP and SIP cleaning.

Outer O-ring gaskets 49, 49 provide seals between the mounting rings and the outer faces 44b, 44b of the windows. These gaskets are received in O-ring grooves or seats 52 which are formed in the inner faces 41a of the mounting ring bases and surround apertures 42.

When mounting screws 43 are tightened to bring the inner faces of the mounting rings into firm engagement with the sides 11a, 11b of the flowcell body, O-ring gaskets 46 and 49 are compressed in a controlled manner to provide tight seals on both sides of the windows which are clamped between the O-rings, with no contact between the windows and the walls of the cell body and mounting rings.

Light source 16 and detector 17 have modular housings which are mounted on the mounting rings on opposite sides of the flowcell. Each housing has a cylindrical side wall 51 and a circular end wall 52, with a neck portion 53 of reduced diameter which fits over the mounting flange 44 of the mounting ring. The housings are affixed to the window mounts by conically tapered set screws 54 which are threadedly mounted in the neck portions and received in conically tapered sockets 56 in the mounting flanges. The set screws and sockets are spaced 120 degrees apart about optical axis 15 and ensure proper alignment of the light source and detector, both axially and radially. Sealing between the housings and the mounting rings is provided by O-rings 57 between the neck portions of the housing walls and the mounting flanges.

Hermetically sealed connectors 59 are mounted on the end walls for making electrical connections to the light source and detector within the housings.

The light source and detector can be of any suitable type. In one presently preferred embodiment, the light source is a solid state UV source as described and illustrated in application Ser. No. 12/881,438, filed Sep. 14, 2010, the disclosure of which is incorporated herein by reference, and the detector is a photometric detector assembly with NIST traceable internal calibration filters as described and illustrated in U.S. Pat. No. 6,512,223, the disclosure of which is also incorporated herein by reference.

Air hose fittings 61, 62 are mounted on window rings 39 and on the end walls 52 of the light source and detector housings for connection to an air source for purging the flowcell optics and the housings with air. The air flow is helpful in eliminating potential window fogging and as well as in cooling the source and sensor optics in high temperature applications.

The invention is intended for use primarily with smaller process lines having internal diameters ranging from about 1/16 inch to about 1/4 inch (approximately 1.6 mm to 6.3 mm). Sample chamber 12 preferably has a volume no larger than 0.4 mL, and in one presently preferred embodiment, the volume is 0.35 mL, with an optical pathlength of approximately 1.0 cm between the inner faces of windows 38, 38. In low pressure and/or low flow applications, the process sample is introduced into the flowcell in an upward direction through the fitting 19 on the lower side of the flowcell body to ensure that the sample chamber is filled and free of air pockets and to present a representative sample to be analyzed.

The invention has a number of important features and advantages. It provides an inline optical sensor with a small sample chamber that can be used in low pressure and/or low flow applications. With the interchangeable fittings, the inline sensor can be utilized with process lines of different sizes and types, and the doubly tapered chamber with a diameter that increases toward the middle of the chamber ensures proper drainage for the smaller flow lines, eliminates air pockets in the sample area, and limits pressure drop in the lines. The controlled O-ring gasket compression with which the flowcell is sealed ensures tight, leak-proof seals throughout the flowcell. The modular housings maintain proper optical alignment of the light source and detector when attached to the flowcell mounting rings. They also provide thermal isolation and lower thermal conduction from the flowcell, allowing the sensor to be employed in high temperature applications up to about 150° C.

It is apparent from the foregoing that a new and improved micro volume inline optical sensor has been provided. While only certain presently preferred embodiments have been described in detail, as will be apparent to that familiar with the art, certain changes and modifications can be made without departing from the scope of the invention as defined by the following claims.

The invention claimed is:

1. A micro volume inline optical sensor, comprising: a flowcell having a body with monitoring ports aligned along an optical axis on opposite sides of the body, a sample chamber within the body between the ports with a side wall having oppositely inclined frusto-conical sections which are disposed concentrically of the optical axis, increase in diameter toward each other from opposite ends of the chamber, and come together at a junction between the ends where the diameter of the chamber is the greatest, a flow passageway passing through the body and intersecting the sample chamber where the diameter is the greatest, mounting rings disposed coaxially of the optical axis on the opposite sides of the body, and a light source and an optical detector mounted on the mounting rings in alignment with each other and with the sample chamber along the optical axis.

2. The optical sensor of claim 1 wherein the flow passageway has a diameter of approximately 1.6 mm to 6.4 mm, and the sample chamber has a volume of 0.4 mL or less.

3. The optical sensor of claim 1 wherein the light source is a solid state UV source.

4. The optical sensor of claim 1 wherein the detector is a photometric detector with NIST traceable calibration filters.

5. The optical sensor of claim 1 including interchangeable fittings at the ends of the flow passageway for connecting product lines of different diameters and/or types to the flowcell.

6. The optical sensor of claim 1 wherein the flow passageway has an inlet section that intersects the sample chamber from below.

7. The optical sensor of claim 1 wherein the wall sections are inclined at an angle of 10 degrees to the optical axis.

8. The optical sensor of claim 1 wherein the flowcell is sealed with controlled O-ring gasket compression.

9. A micro volume inline optical sensor, comprising: a flowcell having a body with monitoring ports aligned on an optical axis and opening through opposite sides of the body, a sample chamber within the body between the ports with open ends facing the ports, a flow passageway passing through the body and the chamber in a direction generally perpendicular to the optical axis, the sample chamber increasing in diameter from the ends of the chamber toward the flow passageway and the flow passageway intersecting the chamber where the diameter of the chamber is the greatest optically transparent windows in the monitoring ports adjacent to the open ends of the chamber, inner sealing gaskets encircling the open ends of the chamber between inner faces of the windows and the body, mounting rings affixed to the body adjacent to the monitoring ports, outer sealing gaskets between the mounting rings and outer faces of the windows, the mounting rings being in firm contact with the sides of the body with the inner and outer sealing gaskets compressed in a controlled manner to provide tight seals on both sides of the windows with no contact between the faces of the windows and the body and the mounting rings, and a light source and an optical detector mounted on the mounting rings in alignment with each other and with the sample chamber along the optical axis.

10. The optical sensor of claim 9 wherein the flow passageway has a diameter of approximately 1.6 mm to 6.4 mm, and the sample chamber has a volume no larger than 0.4 mL, with an optical pathlength approximately of 1 cm between the windows.

11. The optical sensor of claim 9 wherein the light source is a solid state UV source.

12. The optical sensor of claim 9 wherein the detector is a photometric detector with NIST traceable calibration filters.

13. The optical sensor of claim 9 including interchangeable fittings at the ends of the flow passageway for connecting product lines of different diameters and/or types to the flowcell.

14. A micro volume inline optical sensor, comprising: a flowcell having a body with monitoring ports aligned on an optical axis and opening through opposite sides of the body, a sample chamber within the body between the ports with open ends facing the ports and side wall having oppositely inclined frusto-conical sections which are disposed concentrically of the optical axis, increase in diameter toward each other from opposite ends of the chamber, and come together at a junction between the ends where the diameter of the chamber is the greatest, a flow passageway passing through the body and intersecting the sample chamber where the diameter is the greatest, optically transparent windows in the monitoring ports adjacent to the open ends of the chamber, inner sealing gaskets encircling the open ends of the chamber between inner faces of the windows and the body, mounting rings affixed to the body adjacent to the monitoring ports, outer sealing gaskets between the mounting rings and outer faces of the windows, and a light source and an optical detector mounted on the mounting rings in alignment with each other and with the sample chamber along the optical axis.

15. The optical sensor of claim 14 wherein the inner and outer sealing gaskets are under controlled compression with facing surfaces of the mounting rings and the flowcell body in firm contact with each other.

16. The optical sensor of claim 9 wherein the monitoring ports have annular rear walls with seats surrounding the open ends of the sample chamber in which the inner sealing gaskets are received.

17. The optical sensor of claim 16 where portions of the rear walls are cut away between the gasket seats and the open ends of the sample chamber so that portions of the gaskets are exposed to liquid in the chamber.

18. The optical sensor of claim 15 wherein the windows are clamped between the O-rings, with no contact between the windows and the facing surfaces of the flowcell body and mounting rings.

19. The optical sensor of claim 14 wherein the flow passageway has a diameter of approximately 1.6 mm to 6.4 mm, and the sample chamber has a volume no larger than 0.4 mL, with an optical pathlength of approximately 1 cm between the windows.

* * * * *